US010842590B2

(12) United States Patent
Themelis (10) Patent No.: US 10,842,590 B2
(45) Date of Patent: Nov. 24, 2020

(54) MEDICAL OBSERVATION APPARATUS WITH A MOVABLE BEAM DEFLECTOR AND METHOD FOR OPERATING THE SAME

(71) Applicant: LEICA INSTRUMENTS (SINGAPORE) PTE. LTD., Singapore (SG)

(72) Inventor: George Themelis, Lindau (DE)

(73) Assignee: Leica Instruments (Singapore) Pte. Ltd., Singapore (SG)

(*) Notice: Subject to any disclaimer, the term of this patent is extended or adjusted under 35 U.S.C. 154(b) by 0 days.

(21) Appl. No.: 16/274,310

(22) Filed: Feb. 13, 2019

(65) Prior Publication Data

US 2019/0262093 A1    Aug. 29, 2019

(30) Foreign Application Priority Data

Feb. 23, 2018    (EP) .................................... 18158421

(51) Int. Cl.
*H04N 5/247*    (2006.01)
*A61B 90/00*    (2016.01)
(Continued)

(52) U.S. Cl.
CPC .............. *A61B 90/37* (2016.02); *A61B 90/00* (2016.02); *A61B 90/20* (2016.02); *A61B 90/25* (2016.02); *A61B 90/361* (2016.02); *G02B 21/0012* (2013.01); *G02B 21/368* (2013.01); *G02B 26/0816* (2013.01); *G06F 3/013* (2013.01);
(Continued)

(58) Field of Classification Search
None
See application file for complete search history.

(56) References Cited

U.S. PATENT DOCUMENTS

2003/0112509 A1*   6/2003   Takahashi .......... G02B 21/0012
                                                                359/466
2004/0196553 A1   10/2004   Banju et al.
(Continued)

FOREIGN PATENT DOCUMENTS

JP           2006218105 A       8/2006

*Primary Examiner* — Christopher G Findley
(74) *Attorney, Agent, or Firm* — Hodgson Russ LLP (57) ABSTRACT

Medical observation apparatus (1) and method for observing an object or patient (67) in an operation area (21). Solutions of the art (3, 5) do not allow displaying further information, are expensive, bulky and non-intuitive. The inventive apparatus (1) overcomes these problems by comprising: an image acquisition assembly (41) with a camera subassembly (43) comprising at least one viewing camera (9) with a field of view (85) and an optical camera axis (75) for acquiring interoperative image data (83); a deflector subassembly (47) for deflecting the optical camera axis (75) into an optical viewing axis (77) directed towards the operation area (21), the deflector subassembly (47) comprising at least one optical beam deflector (71) and being arranged between the viewing camera (9) and the operation area (21), wherein the viewing camera (9) and the at least one optical beam deflector (71) are movable with respect to one another; and an image display assembly (37) comprising at least one monitor arrangement (35) for displaying the interoperative image data (83), the monitor arrangement (35) being visible at least from a user's observation position (29).

9 Claims, 5 Drawing Sheets

(51) Int. Cl.
*H04N 5/232* (2006.01)
*G02B 26/08* (2006.01)
*G06F 3/01* (2006.01)
*G02B 21/00* (2006.01)
*A61B 90/25* (2016.01)
*G02B 21/36* (2006.01)
*A61B 90/20* (2016.01)
*H04N 13/204* (2018.01)
*G02B 21/24* (2006.01)
*A61B 34/30* (2016.01)

(52) U.S. Cl.
CPC ......... *H04N 5/23299* (2018.08); *H04N 5/247* (2013.01); *A61B 34/30* (2016.02); *A61B 2090/368* (2016.02); *A61B 2090/3618* (2016.02); *A61B 2090/371* (2016.02); *A61B 2090/373* (2016.02); *G02B 21/24* (2013.01); *H04N 13/204* (2018.05)

(56) References Cited

U.S. PATENT DOCUMENTS

2006/0176242 A1   8/2006   Jaramaz et al.
2015/0085095 A1   3/2015   Tesar
2016/0142683 A1   5/2016   Seeselberg et al.
2017/0336620 A1   11/2017  Kato
2018/0368656 A1*  12/2018  Austin ................. A61B 1/0005

* cited by examiner

MEDICAL OBSERVATION APPARATUS WITH A MOVABLE BEAM DEFLECTOR AND METHOD FOR OPERATING THE SAME

CROSS REFERENCE TO RELATED APPLICATIONS

This application claims priority of European patent application number 18158421.0 filed Feb. 23, 2018, the entire disclosure of which is incorporated by reference herein.

FIELD OF THE INVENTION

The invention relates to a medical observation apparatus, in particular a surgical microscope, for observing an object in an operation area from a user's observation position during surgery and to a method for observing an object in an operation area during surgery from a user's observation position.

BACKGROUND OF THE INVENTION

In the prior art, medical observation apparatuses are known, for example surgical microscopes or robotic arm-based digital imaging systems, as well as methods for operating these. The surgical microscopes, which are routinely used, provide magnification for delicate operations, e.g. neurosurgery. Their eyepieces are, however, all optical and therefore do not allow a modification of the image contents. The eyepieces of surgical microscopes furthermore require an exact positioning and alignment of the observer's eyes relative to the eyepieces.

The relative location and angle of eyepieces and objective lenses result in a limited flexibility, and the field of view and the observation angle need to be selected manually, which interrupts the surgical flow.

Imaging systems for interoperative use utilizing a robotic arm for positioning and aligning a camera relative to the operation area, e.g. to a surgical cavity, as well as methods for operating these, are known in the art. Such systems provide an image of the surgical cavity, wherein the alignment of the robotic arm is in general planned preoperatively. However, robotic arms are expensive, bulky, take up valuable space in an operating room and are only useful for surgical cavities. Use of a robotic arm may result in an unnatural or unusual orientation of the imaging axis.

SUMMARY OF THE INVENTION

An object of the present invention is therefore to provide a medical observation apparatus and a method with more intuitive handling for the surgeon, and which is less costly and less bulky than a robotic arm.

The medical observation apparatus mentioned in the beginning solves the above object by comprising an image acquisition assembly with
  a camera subassembly comprising at least one viewing camera for acquiring interoperative image data, the camera having a field of view and an optical camera axis;
  a deflector subassembly for deflecting the optical camera axis into an optical viewing axis directed towards the operation area, the deflector subassembly comprising at least one optical beam deflector and being arranged between the viewing camera and the operation area,
  wherein the viewing camera and the at least one optical beam deflector are movable with respect to one another.

The inventive medical observation apparatus further comprises an image display assembly with at least one monitor arrangement for displaying the interoperative image data, the monitor arrangement being visible at least from a user's observation position.

The inventive method solves the above object by comprising the steps of deflecting an optical camera axis of at least one viewing camera of a camera subassembly into an optical viewing axis directed towards the operation area; acquiring interoperative image data of the at least one viewing camera; and displaying the interoperative image data on at least one monitor arrangement of the image display assembly.

The inventive medical observation apparatus and the inventive method thus have the advantages that the medical observation apparatus is lighter, less expensive and less bulky than solutions of the art. It may therefore be suitably applied in an existing operative or surgical environment. Furthermore, the inventive medical observation apparatus and method allow for easy adjustment or change of the optical viewing axis without the need to position heavy and/or sensitive elements, such as the robotic arm or a camera. Consequently, the field of view is adjusted very rapidly. The inventive medical observation apparatus is thus more compact than the solutions disclosed in the art, e.g. robotic arm-based digital imaging systems.

The inventive medical observation apparatus and method may be improved by specific embodiments which will be described in the following. Technical features of the embodiments may be arbitrarily combined with each other or omitted if the technical effect obtained by the omitted technical feature(s) is not relevant to the present invention.

The operation area is to be understood as a locally limited area or volume which is under observation. In case of surgery, the operation area corresponds to the part of the patient's body on which surgery is to be performed.

The viewing camera is to be understood as a camera system which may comprise a sensor, e.g. a CCD or CMOS sensor, and an optical system of one or more optical components for imaging the light to be detected onto said sensor. The light to be detected stems from the operation area and may be at least one of transmitted light, reflected light, scattered light or fluorescent light. The measured light may comprise wavelengths in the visible part of the spectrum, i.e. between 400 and 750 nm, but may also comprise near-infrared (NIR) or infrared (IR) components. The corresponding sensor, as well as the optical system, is in general adapted to the operation wavelength or the wavelength range applied. The viewing camera may be a multispectral or hyperspectral camera.

The field of view and optical camera axis are, in general, determined by the optical system as well as by the geometry and size of the sensor of the viewing camera. The camera subassembly may comprise controllers, power input terminals and data input and/or output lines.

The at least one optical beam deflector of the deflector subassembly is preferably positioned such that the optical camera axis is approximately centered with respect to the optical beam deflector. Different embodiments of the at least one optical beam deflector are tiltable mirrors, tunable refractive elements, such as lenses or prisms, as well as catadioptric elements based on combined reflection and refraction.

The interoperative image data may be provided by the viewing camera in order to be displayed on the image display assembly, more particularly on a viewer, such as a screen or monitor.

The image acquisition assembly may further comprise an image acquisition drive system for driving the motion of at least one of the at least one optical beam deflector of the image acquisition assembly and the camera. The image acquisition drive system may comprise an electric motor.

The monitor arrangement may comprise one or more monitors, e.g. monitors arranged for stereoscopic viewing. Furthermore, additional monitors may be provided for general observation by assistants or other observers.

In another exemplary embodiment of the inventive medical observation apparatus, the image display assembly further comprises at least one observation beam deflector device located between the user's observation position and the monitor, wherein the observation beam deflector is for redirecting an optical observation axis from the user's observation position towards the monitor. In the corresponding inventive method, the optical observation axis may thus be redirected from the user's observation position towards the monitor. This embodiment has the advantage that the viewing direction for the surgeon and for the observer does not necessarily have to be oriented directly towards the monitor, as it is redirected towards the monitor by means of the observation beam deflector device. Said observation beam deflector device may be embodied as a mirror, a refractive element, e.g. lenses or prisms, or as a catadioptric element.

An observation drive system may be provided for driving the motion of the at least one observation beam deflector.

The optical eyepiece may, in particular, be directed onto the observation beam deflector device, which is arranged between the observation position and the monitor.

In a further advantageous embodiment, the observation beam deflector and the monitor may be movable with respect to one another. In the corresponding inventive method, the observation beam deflector and the monitor may be moved with respect to one another. The observation beam deflector and the monitor may, in particular, be movable relative to one another with regard to at least one of tilt and distance. Consequently, the monitor may be tiltable and/or shiftable with respect to the observation beam deflector. It is also possible that the observation beam deflector is tiltable and/or shiftable with respect to the monitor.

This embodiment has the advantage that an adjustment of the virtual position of the monitor may be ensured, so that it is not necessary for the user (the viewer, the surgeon) to accurately align his or her eyes relative to the device in order to see the monitor at the desired virtual position. An exact positioning of the eyes with respect to an eyepiece, as in state-of-the-art surgical microscopes, is thus not necessary. Furthermore, the tilt of the monitor allows a projection of the imaged operation area to be introduced or to be removed when viewed by the surgeon.

In another embodiment of the inventive medical observation apparatus, the deflector subassembly may comprise a pair of optical beam deflectors between the viewing camera and the operation area, wherein at least one of the optical beam deflectors of the pair is movable with respect to the other optical beam deflector with regard to at least one of tilt and distance. In the corresponding inventive method, the optical camera axis is deflected by the pair of optical beam deflectors.

This has the advantage that the observation angle, i.e. the angle at which the optical viewing axis is oriented with respect to the operation area, may be selected almost arbitrarily.

The optical beam deflectors of the pair of optical beam deflectors may be embodied as reflective beam deflectors, i.e. mirrors, as refractive beam deflectors, i.e. prisms and the like, or as catadioptric elements. Such optical beam deflectors are lighter and therefore much easier to move and/or tilt than, for instance, the robotic arms, including a viewing camera, disclosed in the art.

Furthermore, a reduction of the footprint, costs and complexity of the medical observation apparatus and the inventive method is also possible when such optical beam deflectors are applied. This results in the advantage that the field of view of the medical observation apparatus may be rapidly adjusted as a medical observation apparatus using those movable optical beam deflectors has a reduced inertia of the movable parts. A deflection mechanism may be much more compact than a robotic arm.

Additionally, almost any camera, illumination system and filters may be applied, as these do not influence the functionality of the optical beam deflector. Hence, sensitive cameras, heavy cameras or cameras that need to be supplied with a cooling agent may also be applied. The camera may remain at a fixed position and only the optical axis of the camera may be adjusted, moved or tilted. Robotic arms disclosed in prior art solutions, however, may be not suitable for handling any camera as they generally have a fixed weight capacity. As the camera provides interoperative image data to the monitor arrangement, the camera applied may operate in a spectral range which is not visible to the human eye. In this case, the interoperative image data is processed and shown in false colors on the monitor of the monitor arrangement. Imaging data in false color may be performed alternatively or additionally.

In a further embodiment of the inventive medical observation apparatus or inventive method, the deflector subassembly may comprise a rotational support assembly for supporting at least one of the camera and the at least one optical beam deflector of the deflector subassembly, the rotational support assembly being rotatable with respect to the rotational axis. The rotational support assembly may be understood as a supporting structure on which at least one of the camera and the at least one optical beam deflector, preferably both beam deflectors of the pair of beam deflectors, are attached.

Preferably, the camera and the at least one optical beam deflector are rotated around the rotational axis together and do not change their relative position to each other during a rotation.

In another embodiment, it is conceivable that the pair of optical beam deflectors may be rotated around the rotational axis, wherein the camera remains at a fixed position.

In a further embodiment of the inventive medical observation apparatus or inventive method, the rotational axis coincides with the optical axis of the camera. In this embodiment, the camera may remain at a fixed position, wherein the at least one optical beam deflector, preferably the pair of optical beam deflectors, are rotated by means of the rotational support assembly.

The rotational axis which corresponds to the optical axis of the camera is located at the at least one optical deflector, preferably at the first optical beam deflector of the pair. In a preferred embodiment, the optical beam deflector has a default orientation whereby it may be oriented to the optical axis of the camera at an angle of approximately 45°.

However, as the at least one optical beam deflector is tiltable and/or rotatable, different default orientations are possible.

The medical observation apparatus may therefore comprise one single stationary rotational axis around which the rotational support assembly may be rotated. The stationary rotational axis may determine the orientation of a support structure, which may be embodied as a rod or similar structure, wherein at said structure a drive system may be attached and supported. The drive system is embodied to drive the rotation of the rotational support assembly around the rotational axis.

The camera and/or the at least one optical beam deflector may therefore be located at a position which coincides with the rotational axis.

As mentioned above, also the camera may be rotatable together with the at least one optical beam deflector by means of the rotational support assembly. In such an embodiment, the section of the operation area, i.e. the interoperative image data, may be rotated with respect to the operation area. If such an embodiment of the rotational support assembly is rotated by approximately 90° in a clockwise direction (as seen from the deflector subassembly towards the operation area), the interoperative image data, more precisely the section of the operation area which is imaged, appears to rotate counterclockwise by approximately 90°.

In order to avoid disturbing the surgeon, whose position, in particular the position of his or her eyes, remains unchanged, a further embodiment of the inventive observation apparatus may comprise a viewing camera which is rotatable around the optical camera axis.

Exemplarily, if additional viewers look at an additional screen, wherein the viewers are standing to the left and/or the right of the surgeon rotated by 90° with respect to the surgeon (facing towards the operation area, i.e. the patient). Such an embodiment would allow to rotate the imaged portion of the operation area by 90° clockwise or anticlockwise in order to correspond to the correct orientation with respect to the viewing direction of the additional viewer.

Similarly, a rotation of the imaged operation area by 180° is also feasible in order to adapt the imaged operation area to match the correct positioning for an additional viewer standing opposite the surgeon and thus facing in the opposite direction.

In a particularly advantageous embodiment of the invention, the rotational axis of the rotational support assembly coincides with the optical axis of the camera, wherein at the position of the optical axis of the camera, a first optical beam deflector is arranged at an angle of approximately 45° with respect to the optical axis of the camera, such that the first optical beam deflector introduces a deflection of the optical axis of the camera by approximately 90°.

The first optical beam deflector is furthermore tiltable around at least one, preferably two optical axes. Such an optical beam deflector therefore allows the direction of the optical axis of the camera to be altered, modified or scanned in two directions. The deflected optical axis of the camera (e.g. deflected by 90°) is preferably directed towards a second optical beam deflector which may also be oriented towards said deflected optical axis of the camera at an angle of approximately 45°.

Consequently, the second optical beam deflector deflects the already deflected optical camera axis into the optical viewing axis which is directed towards the operation area. Such an optical viewing axis may therefore be oriented approximately parallel to the original optical camera axis, wherein both axes are offset from each other by a distance which is determined by the distance between the first and the second optical beam deflector.

Also the second optical beam deflector may be tiltable around two axes, wherein the two tilt axes of the first and/or the second optical beam deflector are preferably located within the plane in which the deflection occurs. The two tilt axes may therefore span a deflection plane in which the deflection (e.g. reflection) may occur.

This has the advantage that a tilt around one of the two axes results in a linear deflection. A linear deflection is to be understood as a deflection of an optical beam or axis wherein the deflected axis remains in a (non-curved) plane.

The tilt axes are preferably orthogonal to each other, such that an almost arbitrary deflection may be achieved by a superpositioning of two tilts around the two independent tilt axes. This allows the optical viewing axis to be positioned at a predetermined angle and at a predetermined position. That is to say that the optical viewing axis may be translated parallel and altered in its angle.

In a further embodiment of the inventive medical observation apparatus, the deflector subassembly may comprise a movable range-setting support system for supporting at least one of the camera and the at least one optical beam deflector of the deflector subassembly and for positioning the at least one optical beam deflector at a variable distance from the camera. In the corresponding inventive method, the distance between the camera and the at least one optical beam deflector is varied using the movable range-setting support system. This embodiment has the advantage that the range of angular positioning of the optical viewing axis with respect to the operation area may be increased.

The optical viewing axis may be understood to have its origin at an optical beam deflector (more precisely the beam deflector which is closest to the operation area if the optical path of detected light and/or illumination is considered). The movable range-setting support system changes the position of said origin. In this regard the term "origin" is to be understood as one predetermined point through which the axis passes. It is not to be understood as the point from which electromagnetic radiation is emitted and starts its propagation. This embodiment therefore allows the possible tilt of the optical viewing axis to be altered and, additionally, to translate the resulting optical viewing axis parallelly by means of the movement via the movable range-setting support system.

Most preferably, the medical observation apparatus or the corresponding method may comprise the pair of optical beam deflectors and the viewing camera having an optical viewing axis which coincides with the rotational axis of the rotational support assembly, wherein in the second optical beam deflector may be positioned at a variable distance from the camera by means of the range-setting support system.

Thus, the distance between the first and second optical beam deflector may be varied. Preferably, the movement initiated by the range-setting support system occurs along the optical camera axis when the viewing camera and one single optical beam deflector are present. The movement may occur along the deflected optical camera axis (i.e. the axis between the first and second optical beam deflector) if a pair of optical beam deflectors is provided.

It is to be noted that the geometrical extent of the optical beam deflectors, as well as their maximum possible tilt around the tilt axes, determine a possible tilt range of the optical path of the light to be provided to the operation area or detected from the operation area.

It is further noted that more than two optical beam deflectors may be applied for directing the beam path, wherein such an assembly does not extend a possible scan range of the system. A medical observation apparatus comprising three optical beam deflectors is actually overdetermined in terms of possible scan directions of the beam path.

The method for adjusting two optical beam deflectors in such a way that an axis of the beam deflected by the beam deflectors will reach a specific point in space with a specific angle is known as "beam walking" or "walking the beam," in particular in laser physics.

The movable range-setting support system may comprise a guiding trail, an elongated guiding recess or a guiding rod or similar, along which at least one of the camera and the at least one optical beam deflector may be moved. An embodiment comprising the guiding recess or a guiding slotted hole may additionally be used to deflect the optical viewing axis through said hole or recess towards the operation area.

In a further embodiment of the inventive medical observation apparatus or the inventive method, the range-setting support system is supported by the rotational support assembly. This has the advantage that the rotation of the deflected camera axis does not misalign the optical beam deflector or the second optical beam deflector during the rotation. The entire range-setting support system is rotated with at least one of the camera and the at least one optical beam deflector of the deflector subassembly.

The range-setting support system may comprise a slider device on which the optical beam deflector is mounted. If a pair of optical beam deflectors is applied, the second optical beam deflector may be mounted on the slider.

In another embodiment of the medical observation apparatus or inventive method, the range-setting support system may comprise a rotational subsystem which is rotatable about a second rotational axis. Said second rotational axis is preferably parallel to the rotational axis of the rotational support assembly but is essentially translated parallel to it.

In a further embodiment, a combined movement of the rotational support assembly and the range-setting support system may be restricted to a movement within a predetermined plane.

In a further advantageous embodiment of the inventive medical observation apparatus or method, the range-setting support system is a radial range-setting support system which is rotatable around a support system axis, wherein the rotation of the radial range-setting support system may be synchronized with the rotation of the rotational support assembly.

This embodiment combines two rotational movements in order to obtain a change in the distance between the optical beam deflector and the camera or between the first and second optical beam deflector. Such synchronization may require an additional rotation of the element, i.e. the optical beam deflector attached at or supported by the radial range-setting support system. Preferably, the optical beam deflector is positioned off-center with respect to the support system axis.

In a further particular advantageous embodiment of the inventive medical observation apparatus, the camera deflector subassembly comprises at least one operational mode in which the optical viewing axis coincides with the optical observation axis. In the corresponding embodiment of the inventive method, the optical viewing axis and the optical observation axis are superimposed or overlaid. This embodiment is particularly advantageous as it allows for intuitive surgery or manipulation of the operation area, as the angle of the observation axis corresponds to the optical observation axis, i.e. the axis along which the user's view is directed.

Thus, the perspective the user is seeing is identical to the perspective that the user would perceive if the user were viewing the operation area directly. However, additionally to the image of the operation area, further information may be displayed on the monitor assembly and may be perceived by the user, e.g. the surgeon.

This operational mode may preferably be set by a further embodiment of the medical observation apparatus or method, which may comprise an eye-tracker arrangement, the eye-tracker arrangement comprising an eye-tracker camera having a field of view directed to the user's observation position and providing eye-tracking data representative of the direction of the optical observation axis, and a motion controller for controlling the position of at least one of the viewing camera, the at least one optical beam deflector of the image acquisition assembly, the monitor arrangement and the at least one observation beam deflector of the image display assembly depending on the eye-tracking data.

This has the advantage that the user's viewing direction is detected by the eye-tracker camera, made available in the form of the eye-tracking data and is provided to (i.e. input) the motion controller which may subsequently adjust the tilt of the at least one observation beam deflector of the image display assembly, and the position and/or tilt of the at least one optical beam deflector based on the eye-tracking data.

As an exemplary non-limiting example, the user may move his or her eyes slightly to the left, which may be detected by the eye-tracker camera. Subsequently, several simultaneous adjustments may be performed during the change of the user's viewing direction.

In order to prevent the user's view from bypassing the monitor assembly (i.e. the user's field of view no longer matches the monitor position), the at least one observation beam deflector may be adjusted such that the monitor assembly remains in the field of view of the user.

At the same time, the rotational support assembly and the range-setting support system may be adjusted in order to position the origin of the optical viewing axis (positioned on the optical beam deflector or the second optical beam deflector) on a virtual extension of the user's optical observation axis, wherein the tilt of the at least one optical beam deflector is applied for adjusting the angle of the optical viewing axis such that it coincides with the extended virtual observation axis of the user.

Furthermore, it is conceivable that the eye-tracker camera may not only be applied for readjusting the optical beam deflector, the monitor arrangement or the at least one observation beam deflector, but may also be applied to control further functions of the medical observation apparatus.

The monitor arrangement may, for instance, project additional information or virtual operation mode switches visible to the surgeon. By directly viewing said additional information/virtual switch for a predetermined time, certain settings of the medical observation apparatus may be adapted or changed. Such settings may, for example, be the light intensity, contrast, magnification, overlapping of additional information retrieved from an MRT measurement, x-ray or fluorescence measurement, rotation of the field of view and the like. Controlling these settings may prevent the surgery from being interrupted.

In a further embodiment of the inventive medical observation apparatus or the inventive method, the image display assembly may comprise a further beam deflector device which is located between the eye-tracking camera and the observation beam deflector for deflecting an optical axis of the eye-tracking camera towards the observation deflector. By such an embodiment, the eye-tracker camera is directed (in terms of its optical axis) towards the observation beam deflector and thus also towards the user's eyes. The eye-tracker camera therefore directly points towards the user, which facilitates the calibration and detection of the direction in which the user is looking (in other words, mimics the user's angle of vision).

The eye-tracking camera may be embodied as a camera operating in the near-infrared spectrum so that the user, e.g. the surgeon, is not distracted. The further beam deflector may be embodied as a semi-transparent member or a dichroic mirror which solely reflects near-infrared radiation, but which is preferably completely transparent in order to allow transmission of the illumination light and/or the light to be detected (which stems from the operation area). The further beam deflector therefore ensures good optical access to the user's eyes without distracting the user.

In another embodiment of the inventive medical observation apparatus or method, the viewing camera and the at least one optical beam deflector are positioned with respect to each other based on 3D camera data provided by a 3D camera system.

In particular during surgery in a deep surgical cavity, e.g. during neurosurgery, a 3D camera system may be applied to detect so-called landmarks or special structures of the operation area in order to adjust the viewing camera such that it is directed directly into the deep surgical cavity. For example, a tube may be used to support the walls of the surgical cavity, wherein the readout of the position of the tube may be used to align the medical observation apparatus' optical viewing axis, such that the medical observation apparatus is directed straight into the narrow surgical cavity.

This alignment is generally a time-consuming process if carried out manually by the surgeon. It is thus advantageous if the positioning of the viewing camera, more particularly the positioning of the optical viewing axis towards the operation area, is performed automatically based on the 3D camera data.

The 3D camera system may comprise two 3D cameras operating in the visible, the near-infrared or even the infrared spectrum. Specially prepared detection landmarks, marked or tagged areas or operative tools may be applied to position the optical camera axis such that it is directed into the deep surgical cavity.

In the following, the present invention is described using accompanying figures which show specific embodiments of the inventive medical observation apparatus. The corresponding embodiments of the inventive method are covered by the description of the respective apparatus. The figures show purely exemplary embodiments, wherein specific technical features of the embodiments may be arbitrarily combined with each other or even omitted if the technical effect obtained by the omitted technical features is not relevant to the present invention. Same technical features and technical features having the same technical effect will be denoted using the same reference numeral. A repetitive description will be omitted, while differences in technical features between two figures will be emphasized.

DETAILED DESCRIPTION OF THE INVENTION

Figure 1A:
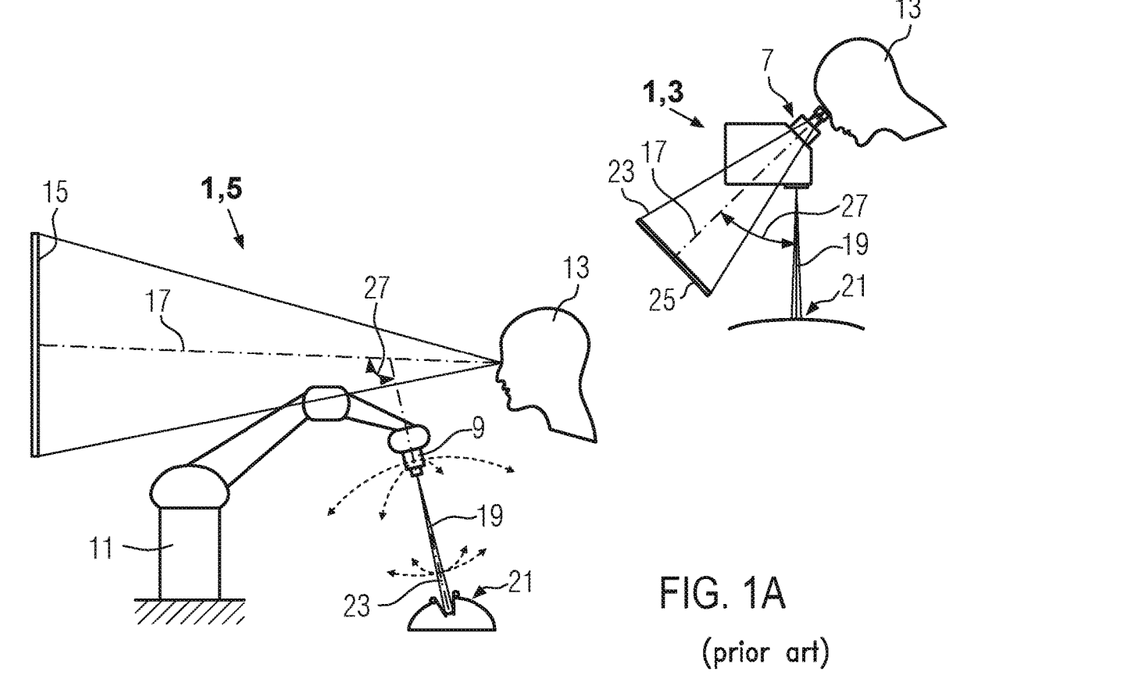
FIGS. 1A and 1B: prior art solutions of medical observation apparatuses and the first embodiment of the inventive medical observation apparatus.

FIG. 1A shows medical observation apparatuses 1 of the art. These may be embodied as a surgical microscope 3, which may be equipped with an eyepiece 7.

Another embodiment of the medical observation apparatus 1 of the art is a robotic arm-based system 5 which comprises a viewing camera 9 which is positioned by means of a robotic arm 11. The robotic arm 11 shown in FIG. 1A is merely exemplary, i.e. a robot arm having a different number of axes may be applied.

A surgeon 13 (or observer, or user) either looks through the eyepiece 7 or onto a display 15. Each of the prior art solutions comprises an optical observation axis 17 which is defined by the surgeon 13. Each system furthermore comprises an optical viewing axis 19 which is directed towards an operation area 21. It is to be noted that each axis 17, 19 is centered within a bundle of rays 23.

FIG. 1A shows that, in the case of the surgical microscope 3, the disadvantage arises that the virtual image 25 as seen by the surgeon 13 only shows the operation area 21, and the optical observation axis 17 is oriented at an observation deviation angle 27 to the optical viewing axis 19. In case of the robotic arm-based system 5 the observation deviation angle 27 may be much larger than in the case of a surgical microscope 3. This may be one reason why operating such a robotic arm-based system 5 is considered less intuitive and requires special training. Furthermore, the robotic arm 11 requires a large space in the operation room to accommodate it, as well as the infrastructure necessary for its operation.

Figure 1B:
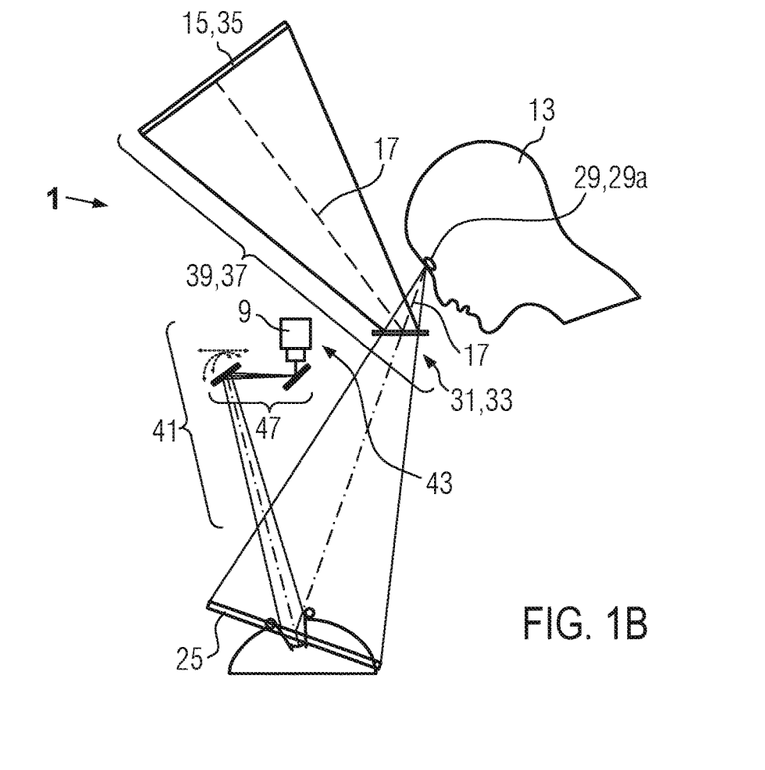

FIG. 1B shows a medical observation apparatus 1 according to the invention. The surgeon 13 is located at the user's observation position 29, which is, in particular, determined by the position of his or her eyes 29a. The surgeon 13 looks at an observation beam deflector device 31 which is embodied as a mirror 33 in the embodiment shown.

The observation beam deflector 31 redirects the optical observation axis 17 from the user's observation position 29 towards a monitor arrangement 35. The monitor arrangement 35 may be embodied as a display 15 and dependent on the orientation of the observation beam deflector 31. The monitor arrangement 35 is located at a different position than the virtual image 25 as seen by the surgeon 13.

The at least one observation beam deflector 31 (different embodiments may comprise more than one observation beam deflector 31), the optical observation axis 17 as well as the monitor arrangement 35 and possible further optical elements (not shown) form an image display assembly 37 acting as the interface 39 to the medical observation apparatus 1 for the surgeon 13, user or observer.

The inventive medical observation apparatus 1 further comprises an image acquisition assembly 41 with a camera subassembly 43, which in an easy embodiment—as shown in FIG. 1B—merely comprises the viewing camera 9, and with a deflector subassembly 47 which will be described in more detail with reference to FIG. 2B.

Figures 2A, 2B:
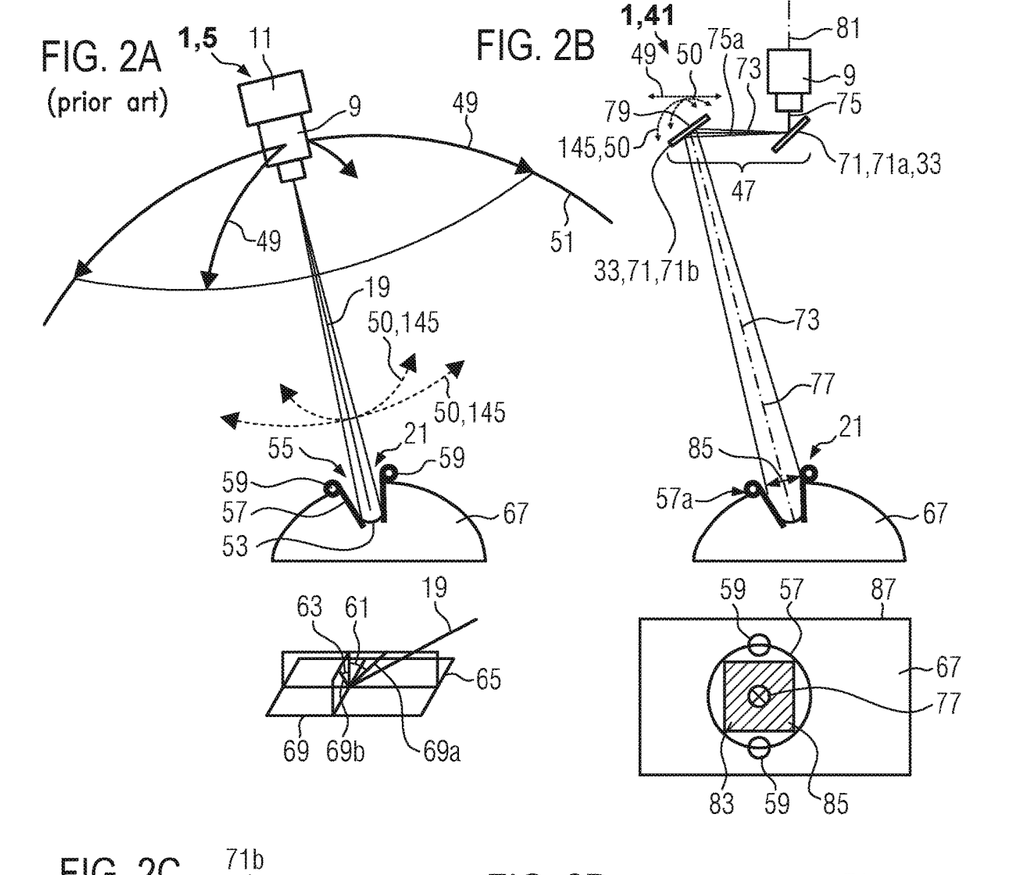
FIGS. 2A and 2B: a magnified view of the working principle of the prior art solution applying a robot arm-based system compared with the inventive image acquisition assembly of the inventive medical observation apparatus.

FIG. 2A shows a magnified view of the working principle of the prior art solution applying a robot-based system 5 compared to the inventive image acquisition assembly 41 of the inventive medical observation apparatus 1 (FIG. 2B).

In the prior art solution, the viewing camera 9 is attached to the robotic arm 11 and may be freely translated and rotated in the three-dimensional space. It is therefore possible to move the viewing camera 9 on trajectories 49 which may be located on a sphere 51.

Furthermore, the viewing camera 9 may be tilted, which is indicated by tilt trajectories 50, which are marked using dashed lines. The tilt trajectories 50 therefore indicate a possible tilt 145. A tilt 145 of the viewing camera 9 allows the user 13 to change at least one, preferably two incident angles 61, 63 at which the optical viewing axis 19 is oriented to an operation plane 65. The incident angles 61, 63 are indicated separately. It is to be noted that the operation plane 65 is fixed in space with respect to a patient 67 and preferably comprises the center 53 of the sphere 51, i.e. the viewing camera 9 and its optical system (not shown) is adjusted, i.e. focused to the operation plane 65. The schematic drawing shows a first projection 69a and a second projection 69b of the exemplary optical viewing axis 19, wherein a first incident angle 61 and a second incident angle 63 are obtained. The prior art system allows almost any arbitrary combination of incident angles 61, 63.

The center 53 of said sphere 51 is located in the operation area 21, wherein the operation area 21 is a deep surgical cavity 55 which is kept open by a tube 57. The tube 57 comprises 3D markers 59, via which the viewing camera 9 may be positioned with respect to the operation area 21.

It can be seen that, in the prior art shown in FIG. 2A, the whole viewing camera 9 is moved by the robotic arm 11, wherein a weight limit may apply which may render impossible the application of certain heavy cameras 9, sensitive cameras 9 as well as cameras requiring delicate infrastructure e.g. for cooling and the like.

FIG. 2B shows the inventive image acquisition assembly 41 comprising the viewing camera 9 and the deflector subassembly 47 previously mentioned. The deflector subassembly 47 comprises two optical beam deflectors 71, which, along an optical path 73 from the viewing camera 9 to the patient 67, may be referred to as a first optical beam deflector 71a and a second optical beam deflector 71b.

The first optical beam deflector 71a and/or the second optical beam deflector 71b may be embodied as a mirror 33, wherein said mirrors 33 are arranged anti-parallel to each other. The viewing camera 9 comprises an optical camera axis 75 which indicates the direction towards which the viewing camera 9 is directed.

The first optical beam deflector 71a is oriented towards the optical camera axis 75 at an angle of approximately 45°, such that a deflected axis 75a is oriented essentially perpendicular to the optical camera axis 75.

In the embodiment shown in FIG. 2B, the second optical beam deflector 71b is movable along a trajectory 49, which is, however, linear in the embodiment shown. Additionally, the second optical beam deflector 71b is tiltable, as indicated by the tilt trajectories 50 which are plotted with a dashed line.

The optical path 73 between the second optical beam deflector 71b and the patient 67 is referred to as the optical viewing axis 77, which is a directed towards the operation area 21.

Contrary to the prior art solutions, the viewing camera 9 remains at a fixed position, wherein the movement (translation and/or tilt) of the second optical beam deflector 71b is applied to linearly translate and/or angularly direct the optical viewing axis 77.

In another embodiment of the inventive image acquisition assembly 41 of the medical observation apparatus 1, also the first optical beam deflector 71a may be movable and/or tiltable.

The position at which the optical path 73 hits the second optical beam deflector 71b may be referred to as origin 79. In this regard, the term "origin" is to be understood as one predetermined point through which the optical viewing axis 77 passes. It is not to be understood as the point from which electromagnetic radiation (light reflected, scattered or emitted from the patient 67) is generated and starts its propagation.

In the embodiment of FIG. 2B, the second optical beam deflector 71b is only movable along one trajectory 49. In different embodiments, a movement along a trajectory 49 perpendicular to the one shown in the figure may be possible. Such an embodiment, however, requires a readjustment of the angle of the first optical beam deflector 71a in order to maintain the optical path 73 on the second optical beam deflector 71b. Furthermore, different embodiments may comprise a tiltable first optical beam deflector 71a.

Additionally, the viewing camera 9 may be rotatable around an optical camera axis 81.

In the configuration shown in FIG. 2B, the viewing camera 9 acquires interoperative image data 83 from the camera's field of view 85, which is shown in the figure as a distance but which may be represented by a two-dimensional plane extending into the drawing plane.

For the sake of clarity, a rectangle 87 indicates a view onto the patient 67 along the optical viewing axis 77. The rectangle 87 shows the tube 57 as well as the two 3D markers 59, in between which the field of view 85 of the viewing camera 9 is located. The field of view is indicated by shading and does not encompass the upper portion 57a of the tube 57. The latter may, however, be the case in different embodiments. The interoperative image data 83 corresponds to a representation of a light distribution in the operation area 21 covered by the field of view 85.

When a surgeon is positioned as indicated in FIG. 1B, the portion shown in the rectangle 87 is to be rotated by 90° in the clockwise direction. By rotating the viewing camera 9 around the optical camera axis 81, the field of view 85 and thus also the interoperative image data 83 may also be rotated. This allows for intuitive observation from a position other than that shown in FIG. 1B.

Figure 2C:
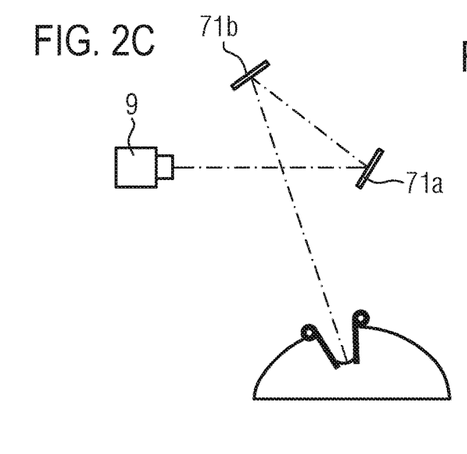
FIGS. 2C and 2D: further possible setups for the inventive image acquisition assembly.
Figure 2D:
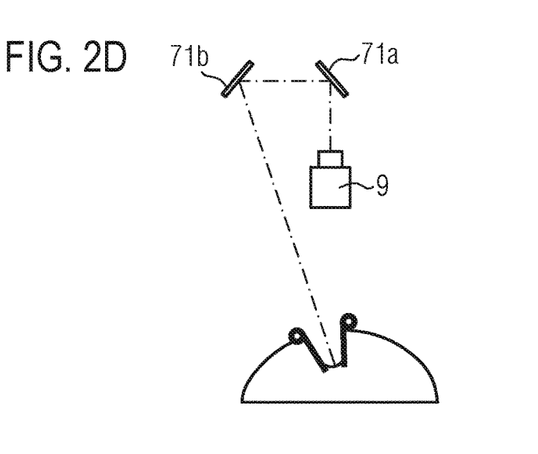

In FIGS. 2C and 2D, different configurations of the inventive image acquisition assembly 41 are shown. In particular the position of the viewing camera 9 may determine an initial orientation of the first optical beam deflector 71a and the second optical beam deflector 71b. Additionally, a third optical beam deflector (not shown) may also be incorporated in order to allow the application of a viewing camera 9 which is located at a position different to that shown and which may not be relocated because of its weight and/or its mechanical stability requirements.

Figure 3:
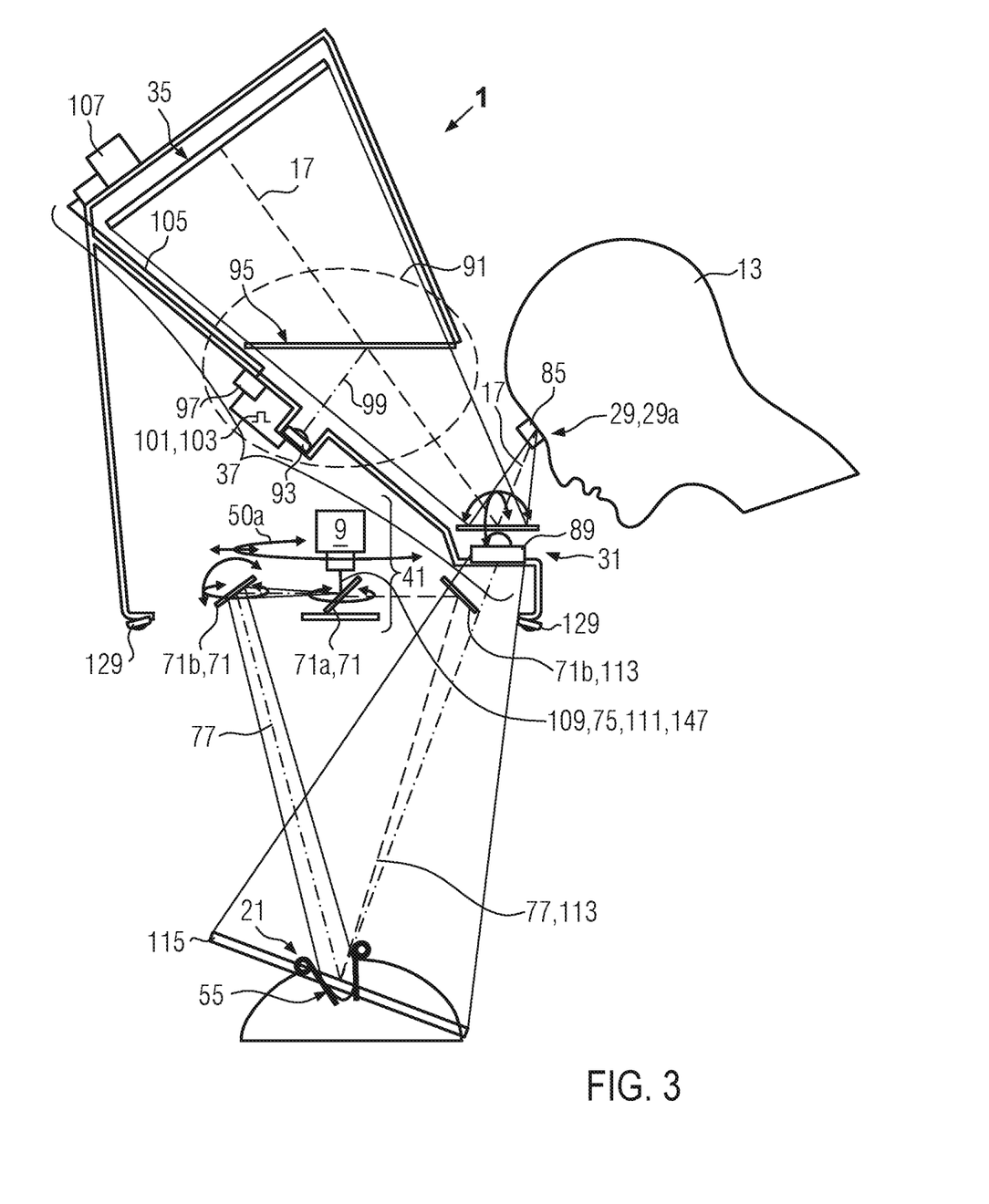
FIG. 3: a second embodiment of the inventive medical observation apparatus.

In FIG. 3, a further embodiment of the inventive medical observation apparatus 1 is shown. The image display assembly 37 corresponds to the one shown in FIG. 1B, wherein an additional gimbal mount 89 is shown which forms part of the observation beam deflector 31. The gimbal mount 89 allows for variation of the redirecting of the user's optical observation axis 17 towards the monitor arrangement 35.

The image display assembly 37 additionally comprises an eye-tracker arrangement 91, which comprises an eye-tracker camera 93, a further beam deflector device 95 which is located between the eye-tracking camera 93 and the observation beam deflector 31, and a motion controller 97.

The eye-tracking camera 93 also has a field of view 85 which is directed to the user's, i.e. the surgeon's 13 observation position 29, in particular the eyes 29a of the surgeon 13. The eye-tracker camera 93 also has an optical camera axis which will be referred to as the 3D tracker axis 99. The 3D tracker axis 99 is deflected by the further beam deflector device 95 and the observation beam deflector 31 such that the eyes 29a of the surgeon 13 are detected, wherein a changed viewing direction of the surgeon 13 is detectable by the eye-tracker arrangement 91.

Thus, the eye-tracker camera 93 provides eye-tracking data 101 which is indicated in the drawing by a single rectangular impulse 103 and which is representative of the direction of the optical observation axis 17. The eye-tracking data 101 may be provided to the motion controller 97.

The motion controller 97 may comprise a data line 105 for providing the eye-tracking data 101 to a deflection controller 107. The motion controller 97 thus controls the position of at least one of the viewing camera 9, the at least one optical beam deflector 71 of the image acquisition assembly 41, the monitor arrangement 35 and the at least one observation beam deflector 31 of the image display assembly 37.

For the sake of clarity, control data lines, drive systems as motors, power supply lines and the like, which are applied to control said above listed elements, are not shown in the figure.

In the embodiment of the medical observation apparatus 1 shown in FIG. 3, also the first optical beam deflector 71a is tiltable, wherein a tilt axis 109 intersects with the optical camera axis 75. The tilt axis 109 is preferably positioned in the reflective surface of the first optical beam deflector 71a.

Additionally, the first optical beam deflector 71a and the second optical beam deflector 71b may be collectively rotated around a rotational axis 111 which coincides with the optical camera axis 75. This collective rotation is indicated by a rotational support trajectory 50b. A rotation 147 occurs around the rotational axis 111.

By means of this collective rotation, the optical viewing axis 77, which is directed towards the operation area 21, in particular the deep surgical cavity 55, may be rotated such that a cone or a truncated cone of possible orientations of the optical viewing axis 77 is obtained. A second possible position 113 resulting from this rotation is indicated in the figure for the second optical beam deflector 71b and the optical viewing axis 77.

The figure also shows a virtual location 115 of the monitor arrangement 35. This virtual location 115 overlaps with the operation area 21 and thus allows for intuitive handling by the surgeon 13. The virtual location 115 indicates the position at which the surgeon 13 apparently perceives the monitor arrangement 35.

Figure 4:
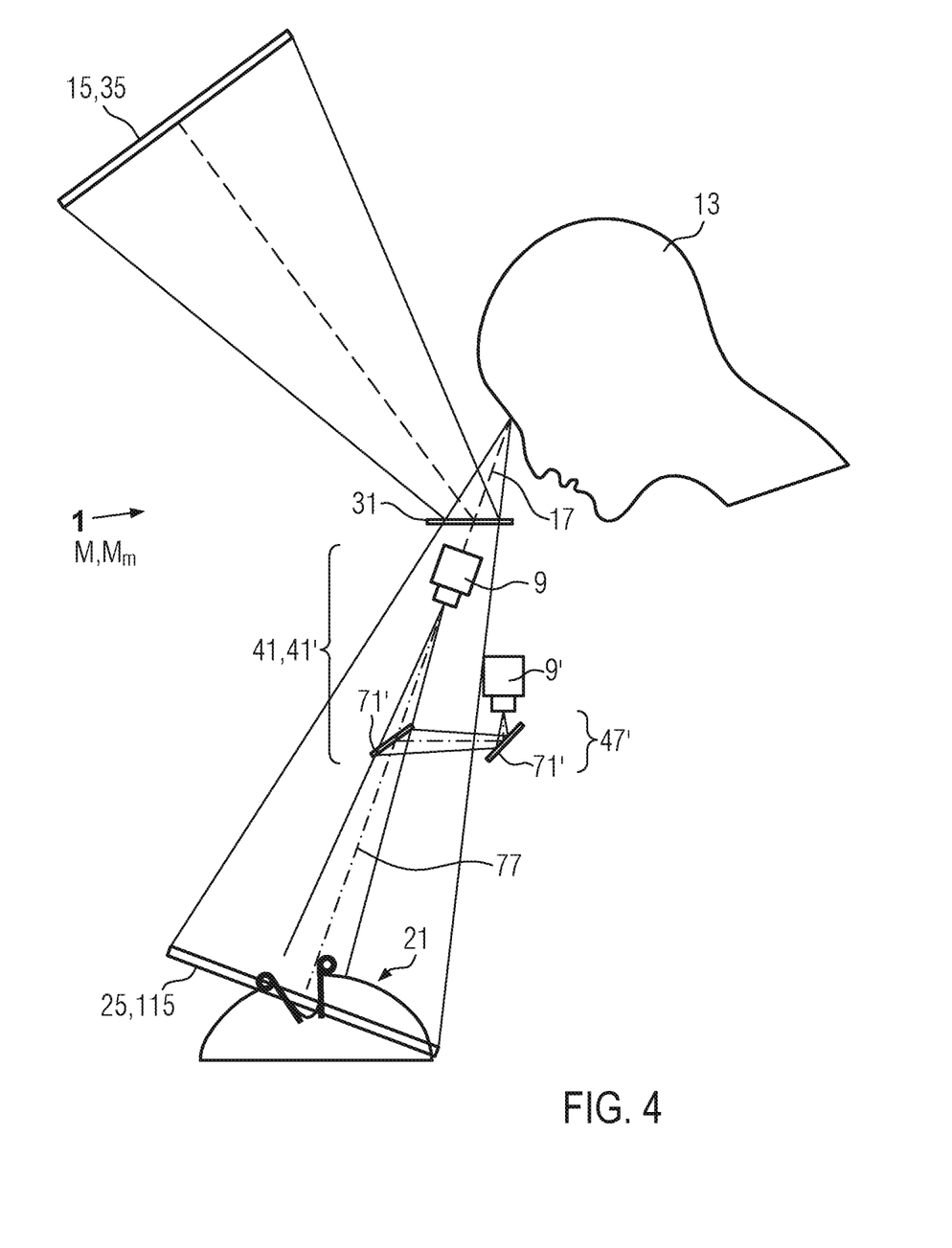
FIG. 4: another embodiment of the inventive medical observation apparatus and a particular operation mode of the same.

FIG. 4 shows one particular operation mode M of the inventive medical observation apparatus 1, namely a merged operation mode $M_m$, which will be described in the following.

It is to be noted that FIG. 4 shows an embodiment of the medical observation apparatus 1 which differs from the previously shown embodiments in that the viewing camera 9 directly views the operation area 21. However, the merged operation mode $M_m$ may also be set by any of the previously shown embodiments of the medical observation apparatus 1, as is indicated by a viewing camera 9' and two optical beam deflectors 71' of the deflector subassembly 47'.

The merged operation mode $M_m$ is particularly advantageous as in this operation mode M, the optical viewing axis 77 of the image acquisition assembly 41 (or 41' if the optical beam deflectors 71' and viewing camera 9' are applied) coincides with the optical observation axis 17 of the user, e.g. the surgeon 13. Consequently, the virtual location 115 of the display 15 of the monitor arrangement 35 may coincide with the position of the virtual image 25 as seen by the surgeon 13. In other words, the surgeon 13 is provided with interoperative image data 83 shown on the display 15 which may exactly match the surgeon's 13 view if no observation beam deflector 31 or image acquisition assembly 41, 41' would be present, at least in terms of an observation angle at which the operation area 21 is observed.

Although surgeons 13 are trained to "transpose" the movements of surgical instruments, e.g. scalpels etc., during an operation, particularly if an endoscope is applied, said merged operation mode $M_m$ mimics the most intuitive way of performing surgery (in which the surgeon 13 apparently directly views the operation area 21).

Figure 5A:
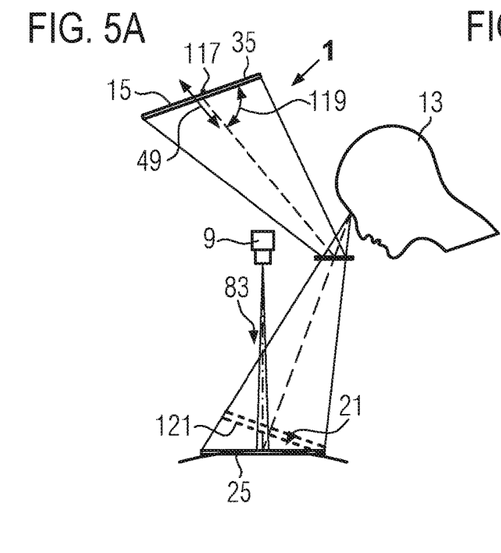
FIGS. 5A and 5B: schematic working principle of different operation modes of the inventive medical observation apparatus.
Figure 5B:
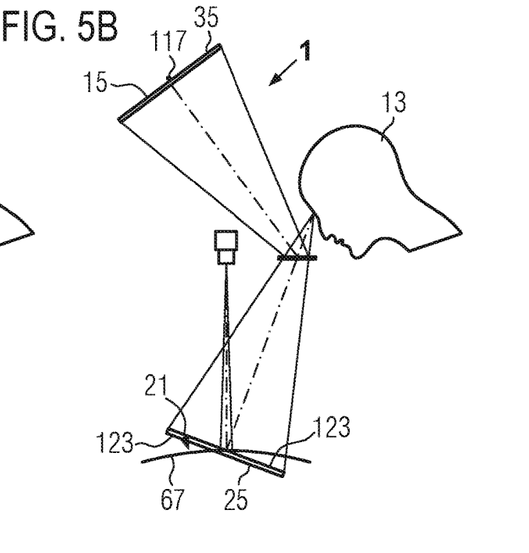

In another embodiment of the inventive medical observation apparatus 1, a monitor arrangement 35 is provided which is tiltable around a monitor rotation axis 117 and/or movable along a trajectory 49. In FIGS. 5A and 5B, such a schematic working principle of the inventive medical observation apparatus 1 is shown.

As can be seen in FIG. 5A, the viewing camera 9 has an optical viewing axis 77 which is oriented perpendicular to the operation area 21. The interoperative image data 83 recorded by the viewing camera 9 is shown on the display 15. As the display 15 is oriented at a tilt angle 119 different than 90°, the virtual image 25 as seen by the surgeon 13 lies in the plane of the operation area 21. The surgeon 13 therefore perceives an image projection 121, which is indicated in the figure by a dashed line. Such a projection 121 slightly distorts the distances and angles of the operation area.

By rotating the display 15 in a counterclockwise direction as shown in FIG. 5B, the virtual image 25 as seen by the surgeon 13 is tilted with respect to the operation area 21, such that no distortion occurs due to the projection 121 (not shown in FIG. 5B as no projection is present). Distances and angles are correctly displayed and seen by the surgeon 13. However, the surgeon 13 may overestimate or underestimate the actual position of the patient 67 if viewing the outlying areas 123 of the virtual image 25.

Figure 6A:
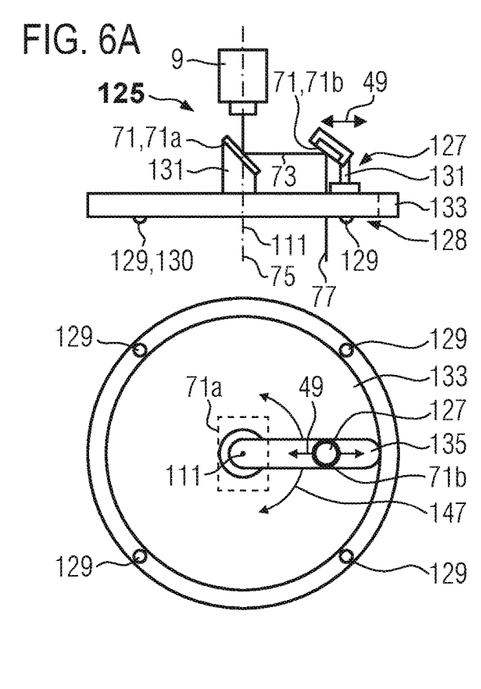
FIGS. 6A and 6B: different embodiments of an inventive rotational support assembly and the range-setting support assembly.
Figure 6B:
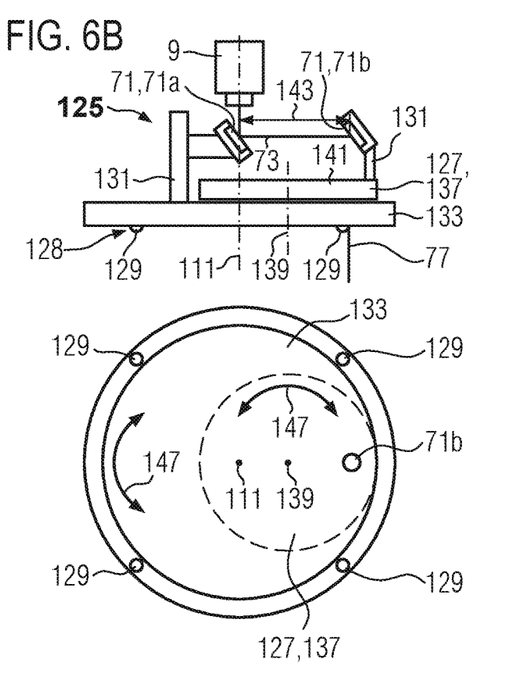

FIGS. 6A and 6B show different embodiments of an inventive rotational support assembly 125 and a range-setting support assembly 127. The viewing direction of the lower panel of both figures is from the operation area 21 along the optical viewing axis 77 towards the at least one optical beam deflector 71. The upper panel of both figures shows a side view of the inventive rotational support assemblies 125.

The rotational support assemblies 125 furthermore comprise a 3D camera system 128 which comprises 3D cameras 129. The 3D cameras 129 are already shown in FIG. 3. The 3D camera system 128 provides 3D camera data 130 which is merely indicated but not further described. The 3D camera system 128 may furthermore comprise a 3D controller (not shown) which calculates a 3D position of elements located in the operation area 21 and provides 3D camera data 130 for controlling and/or repositioning the viewing camera 9 and/or the at least one optical beam deflector 71.

In the embodiment of the rotational support assembly 125 shown in FIG. 6A, the first optical beam deflector 71a and the second optical beam deflector 71b are attached via posts 131 to a rotation base 133 may perform a rotation 147 around the rotational axis 111. As explained above, it is advantageous if the rotational axis 111 corresponds to the optical camera axis 75. A rotation 147 of the rotational support assembly 125 therefore does not change the relative position between the first optical beam deflector 71a and the second optical beam deflector 71b. The viewing camera 9 may also be rotated together with both optical beam deflectors 71.

This embodiment furthermore comprises the range-setting support assembly 127 which comprises a guiding slot 135 along which the post 131 supporting the second optical beam deflector 71b may be moved following the linear trajectory 49.

FIG. 6B shows a further embodiment of the inventive rotational support assembly 125, wherein the range-setting support assembly 127 is embodied as a radial range-setting support system 137. In this embodiment, the first optical beam deflector 71a is supported by the rotation base 133 and rotatable around the rotational axis 111. Also in this embodiment, the viewing camera 9 may be rotatable around the same axis 111. The radial range-setting support system 137 of this embodiment does not perform a linear movement but a rotation 147 around a support system axis 139 which is essentially parallelly offset from the rotational axis 111.

The second optical beam deflector 71b is supported by a post 131 and attached to a support system base 141 of the radial range-setting support system 137.

The rotational support assembly 125 and the radial range-setting support system 137 may be rotated either independently of each other or in a synchronized manner.

In particular, a combination of the rotation 147 of the rotational support assembly 125 and the (off-center) rotation 147 of the radial range-setting support system 137 may change a distance 143 between the first optical beam deflector 71a and the second optical beam deflector 71b.

In order to maintain the optical path 73 on the first optical beam deflector 71a and on the second optical beam deflector 71b, the optical beam deflectors 71 may also be rotatable.

REFERENCE NUMERALS 1 medical observation apparatus
3 surgical microscope
5 robotic arm-based system
7 eyepiece
9, 9' viewing camera
11 robotic arm
13 surgeon
15 display
17 optical observation axis
19 optical viewing axis
21 operation area
23 bundle of rays
25 virtual image
27 observation deviation angle
29 user's observation position
29a eye
31 observation beam deflector
33 mirror
35 monitor arrangement
37 image display assembly
39 interface
41 image acquisition assembly
43 camera subassembly
47, 47' deflector subassembly
49 trajectory
50 tilt trajectory
50a further tilt trajectory
50b rotational support trajectory
51 sphere
53 center
55 deep surgical cavity
57 tube
57a upper portion
59 3D marker
61 incident angle
63 incident angle
65 operation plane
67 patient
69a first projection
69b second projection
71, 71' optical beam deflector
71a first optical beam deflector
71b second optical beam deflector
73 optical path
75 optical camera axis
75a deflected axis
77 optical viewing axis
79 origin
81 optical camera axis
83 interoperative image data
85 field of view
87 rectangle
89 gimbal mount
91 eye-tracker arrangement
93 eye-tracker camera
95 further beam deflector device
97 motion controller
99 3D tracker axis
101 eye-tracking data
103 rectangular impulse
105 data line
107 deflection controller
109 tilt axis
111 rotational axis
113 second position
115 virtual location
117 monitor rotation axis
119 tilt angle
121 image projection
123 outlying area
125 rotational support assembly
127 range-setting support assembly
128 3D camera system
129 3D camera
130 3D camera data
131 post
133 rotational base
135 guiding slot
137 radial range-setting support system
139 support system axis
141 support system base
143 distance
145 tilt
147 rotation
Mm merged operation mode
M operation mode

What is claimed is:

1. A medical observation apparatus (1) for observing an object in an operation area (21) from a user's observation position (29) during surgery, comprising:
   an image acquisition assembly (41) including
   a camera subassembly (43) comprising at least one viewing camera (9) for acquiring interoperative image data (83), the viewing camera (9) having a field of view (85) and an optical camera axis (81); and
   a deflector subassembly (47) for deflecting the optical camera axis (81) into an optical viewing axis (77) directed towards the operation area (21), the deflector subassembly (47) comprising at least one optical beam deflector (71) and being arranged between the viewing camera (9) and the operation area (21),
   wherein the viewing camera (9) and the at least one optical beam deflector (71) are movable with respect to one another; and
   an image display assembly (37) including at least one monitor arrangement (35) for displaying the interoperative image data (83), the monitor arrangement (35) being visible at least from the user's observation position (29);
   wherein the image display assembly (37) further includes at least one observation beam deflector (31) located between the user's observation position (29) and the monitor arrangement (35), wherein the observation beam deflector (31) is for redirecting an optical observation axis (17) from the user's observation position (29) towards the monitor arrangement (35),
   wherein the deflector subassembly (47) comprises a rotational support assembly (125) for supporting at least one of the viewing camera (9) and the at least one optical beam deflector (71) of the deflector subassembly (47), the rotational support assembly (125) being rotatable around a rotational axis (111),
   wherein the deflector subassembly (47) comprises a movable range-setting support assembly (127) for supporting at least one of the viewing camera (9) and the at least one optical beam deflector (71) of the deflector subassembly (47) and for positioning the at least one optical beam deflector (71) at a variable distance (143) from the viewing camera (9),
   wherein the rotational axis (111) coincides with the optical camera axis (81) of the viewing camera (9), and wherein the range-setting support assembly (127) is a radial range-setting support assembly (137) which is rotatable around a support system axis (139), wherein a rotation (147) of the radial range-setting support system is synchronized with a rotation of the rotational support assembly (125).

2. The medical observation apparatus (1) according to claim 1, wherein the observation beam deflector (31) and the monitor arrangement (35) are movable with respect to one another.

3. The medical observation apparatus (1) according to claim 1, wherein the deflector subassembly (47) comprises a pair of optical beam deflectors (71) between the viewing camera (9) and the operation area (21), wherein at least one of the optical beam deflectors (71) of the pair is movable with respect to the other optical beam deflector (71) of the pair with regard to at least one of tilt (145) and distance (147).

4. The medical observation apparatus (1) according to claim 1, wherein the viewing camera (9) is rotatable around the optical camera axis (81).

5. The medical observation apparatus (1) according to claim 4, wherein the range-setting support assembly (127) is supported by the rotational support assembly (125).

6. The medical observation apparatus (1) according to claim 1, wherein the camera deflector subassembly (47) comprises at least one operational mode (Mm) in which the optical viewing axis (77) coincides with the optical observation axis (17).

7. The medical observation apparatus (1) according to claim 1, further comprising an eye-tracker arrangement (91), the eye-tracker arrangement (91) comprising
   an eye-tracker camera (93) having a field of view (85) directed to the user's observation position (29) and for providing eye-tracking data (101) representative of the direction of the optical observation axis (17), and
   a motion controller (97) for controlling the position of at least one of the viewing camera (9), the at least one optical beam deflector (71) of the image acquisition assembly (41), the monitor arrangement (35) and the at least one observation beam deflector (31) of the image display assembly (37) depending on the eye-tracking data (101).

8. The medical observation apparatus (1) according to claim 7, wherein the image display assembly (37) comprises a further beam deflector device (95) which is located between the eye-tracking camera (93) and the observation beam deflector (31) for deflecting an optical axis (99) of the eye-tracking camera (93) towards the observation beam deflector (31).

9. The medical observation apparatus (1) according to claim 1, wherein the viewing camera (9) and the at least one optical beam deflector (71) are positioned with respect to each other based on 3D camera data (130) provided by a 3D camera system (128).

* * * * *